US012691215B2

(12) United States Patent
Yu et al.

(10) Patent No.: US 12,691,215 B2
(45) Date of Patent: Jul. 28, 2026

(54) DELIVERY DEVICE WITH CAM DRIVEN PERISTALTIC PUMP

(71) Applicant: Becton, Dickinson and Company, Franklin Lakes, NJ (US)

(72) Inventors: Bo Yang Yu, Winchester, MA (US); Alessandro Pizzochero, Chelmsford, MA (US); J. Richard Gyory, Sudbury, MA (US); Mark Wood, Sterling, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 535 days.

(21) Appl. No.: 18/030,845

(22) PCT Filed: Oct. 5, 2021

(86) PCT No.: PCT/US2021/053458
§ 371 (c)(1),
(2) Date: Apr. 7, 2023

(87) PCT Pub. No.: WO2022/076337
PCT Pub. Date: Apr. 14, 2022

(65) Prior Publication Data
US 2023/0381407 A1 Nov. 30, 2023

Related U.S. Application Data

(60) Provisional application No. 63/089,922, filed on Oct. 9, 2020.

(51) Int. Cl.
*A61M 5/142* (2006.01)
*A61M 5/145* (2006.01)

(52) U.S. Cl.
CPC ...... *A61M 5/14248* (2013.01); *A61M 5/1452* (2013.01); *A61M 2005/14533* (2013.01); *A61M 2202/0007* (2013.01)

(58) Field of Classification Search
CPC .................... A61M 5/14248; A61M 5/14228; F04B 43/12
See application file for complete search history.

(56) References Cited

U.S. PATENT DOCUMENTS 4,199,307 A 4/1980 Jassawalla
4,909,710 A * 3/1990 Kaplan ................. F04B 43/082
417/474

(Continued)

FOREIGN PATENT DOCUMENTS

CN 1568201 A 1/2005
CN 110870929 A 3/2020

(Continued)

OTHER PUBLICATIONS

International Search Report dated Dec. 22, 2021, which issued in the corresponding PCT Patent Application No. PCT/US2021/053458.

*Primary Examiner* — Laura A Bouchelle
(74) *Attorney, Agent, or Firm* — Dickinson Wright PLLC

(57) ABSTRACT

A delivery device for delivering medicament, such as insulin, to a patient includes a housing and a base enclosing an inner cavity. Enclosed within the housing is a reservoir for containing a medicament, a delivery mechanism for delivering the medicament to the patient, and a pump in fluid communication with the reservoir and delivery mechanism. The base has an integrally formed fluid channel covered by a flexible membrane in fluid communication with the reservoir and the delivery mechanism. A peristaltic pump mechanism includes a cam assembly having a plurality of cams and cam follower assembly with a plurality of protrusions to sequentially engaging the flexible membrane to advance the fluid through fluid channel.

18 Claims, 9 Drawing Sheets

(56)     References Cited

U.S. PATENT DOCUMENTS

| | | | |
|---|---|---|---|
| 5,601,420 A | 2/1997 | Warner et al. | |
| 6,589,229 B1 | 7/2003 | Connelly et al. | |
| 2008/0038128 A1 | 2/2008 | Haar | |
| 2010/0049128 A1 | 2/2010 | Mckenzie et al. | |
| 2010/0174239 A1* | 7/2010 | Yodfat .................... F16L 11/12 | |
| | | | 604/153 |
| 2017/0049960 A1 | 2/2017 | Nguyen | |
| 2018/0272058 A1 | 9/2018 | Pizzochero et al. | |

FOREIGN PATENT DOCUMENTS

| | | | |
|---|---|---|---|
| CN | 216536394 U | 5/2022 | |
| JP | H05-157052 A | 6/1993 | |
| JP | 2005-507688 A | 3/2005 | |
| WO | 1999/11309 A1 | 3/1999 | |

* cited by examiner

DELIVERY DEVICE WITH CAM DRIVEN PERISTALTIC PUMP

RELATED APPLICATIONS

This application is a National Stage Patent Application based on PCT Patent Application No. PCT/US2021/053458, filed Oct. 5, 2021, which claims priority to U.S. Provisional Patent Application Ser. No. 63/089,922, filed Oct. 9, 2020. Each of these applications is hereby incorporated by reference in its entirety.

FIELD OF THE INVENTION

The present invention relates to medical devices, and more particularly, to a medicament delivery device with at least one fluid channel to direct the medicament, such as insulin, to a delivery mechanism for delivering the medicament to a patient. The delivery device includes a cam driven peristaltic pump mechanism.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

An effective method for insulin therapy and managing diabetes is infusion therapy or infusion pump therapy in which an insulin pump is used. The insulin pump is able to provide continuous infusion of insulin to a diabetic patient at varying rates to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

To facilitate infusion therapy, there are generally two types of insulin pumps, namely, conventional pumps and patch pumps. Conventional pumps use a disposable component, typically referred to as an infusion set, tubing set or pump set, which conveys the insulin from a reservoir within the pump into the skin of the user. The infusion set includes a pump connector, a length of tubing, and a hub or base from which a cannula, in the form of a hollow metal infusion needle or flexible plastic catheter, extends. The base typically has an adhesive that retains the base on the skin surface during use. The cannula can be inserted onto the skin manually or with the aid of a manual or automatic insertion device. The insertion device may be a separate unit employed by the user.

Another type of insulin pump is a patch pump. Unlike a conventional infusion pump and infusion set combination, a patch pump is an integrated device that combines most or all of the fluidic components in a single housing. Generally, the housing is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such patch pumps are replaced on a frequent basis, such as every three days, or when the insulin reservoir is exhausted. Otherwise, complications may occur, such as restriction in the cannula or the infusion site.

As patch pumps are designed to be a self-contained unit that is worn by the patient, preferably, the patch pump is small, so that it does not interfere with the activities of the user. Thus, to minimize discomfort to the user, it would be preferable to minimize the overall thickness of the patch pump. However, to minimize the thickness of the patch pump, the size of its constituent parts should be reduced as much as possible.

In current patch pump designs, tubes, such as plastic tubes, are employed as fluid pathways to route fluid flow from one internal component to another. For example, a tube can connect a medicament reservoir with a delivery needle, but the space required to internally house such a tube adds to the overall size of the patch pump. The use of tubes can increase cost and can result in additional complexity during automated device assembly processes. For example, such device assembly includes connecting the tubes, which adds steps to the assembly process. In addition, preventing leaks from such connections can give rise to additional challenges.

Accordingly, a need exists for an improved pump construction and fluid path design for use in a limited space environment, such as in a patch pump device, which can minimize or reduce the overall size and complexity of the device.

SUMMARY

A medication delivery device is provided for delivering a medication from a reservoir to delivery system in a controlled dosage having a pump assembly that does not compromise the medication. The medical delivery device has a cannula or needle as the delivery system that is supplied with the mediation by the pump mechanism.

A feature of the present delivery device, such as a patch pump, has at least one fluid channel to transfer the medicament from a reservoir to a delivery system for administering the medication to the patient. A pump mechanism can be formed with a component part of the delivery device. The pump mechanism provides a pumping action with minimal contact of the medication with the parts of the pump mechanism.

The delivery device includes a medication reservoir, a delivery mechanism for delivering the medication to the patient, and a pump mechanism for delivering the medication from the reservoir to the delivery mechanism. The delivery mechanism is typically a needle or cannula inserted in the patient for intradermal delivery of a medication. The pump mechanism in one embodiment is a peristaltic pump formed with a component of the delivery device. The delivery device in one embodiment includes a base having a channel oriented for extending between the medication reservoir and the delivery mechanism. The channel can be formed by a recess in a surface of a part of the delivery device that extends between a reservoir and the delivery mechanism. A flexible membrane covers the recess to form the closed fluid channel. An actuator assembly having a plurality of actuators to deflect the membrane in sequence to produce a pumping action through the channel.

The actuator assembly can be a cam assembly mounted on a component of the delivery device, such as the base, a plate or the cover. The cam assembly includes a plurality of cam members for actuating a plurality of cam followers to engage the flexible membrane and deflect the membrane into the fluid channel. The cam mechanism is actuated to actuate the cam followers in sequence to deflect the membrane in a manner to produce a pumping action in the fluid channel to propel and pump the medication from the medication reservoir the delivery mechanism.

The pump mechanism in one embodiment includes a plurality of cams and a respective cam follower that contacts and deflects the flexible membrane covering the recess so that the cam and cam followers do not contact the medication to minimize shear stress on the medication and increase stability of the medication. The cam mechanism can be a micro-cam to fit within the available space in the housing of the delivery device.

The pump mechanism in one embodiment includes a plurality of cams having a cam follower, where the cam follower is formed from a stamped metal sheet. The cam followers can be formed as a single unit with a plurality of flexible members forming a cam follower assembly that can be deflected by a cam to independently deflect the membrane covering the fluid channel in a controlled sequence to propel the fluid through the fluid channel. The flexible members can include a protrusion extending toward the membrane to contact the membrane when actuated by the cam. In other embodiments, the a plurality of cams and cam followers are formed as separate units or members where the cam followers are attached to a support. Each cam and cam followers are spaced along the fluid channel where the cam can be operated independently by a control mechanism or control circuit. The cam followers can be separate members and are configured to move in a linear direction perpendicular to the plane of the membrane and the longitudinal dimension of the channel. In one embodiment, the cam followers move only in a linear direction relative to the membrane with no lateral or transverse movement of the cam followers.

The delivery device in one embodiment is configured for delivering a medicament to a patient via a needle or flexible cannula positioned in the patient. The device has a housing, which includes a reservoir for containing the medicament. A first internal space can be sealed from fluid ingress can include one or more components of the delivery device. A second internal space that is not sealed from fluid ingress can include one or more components of the delivery device, such as the pump mechanism. The housing can have a barrier that separates the first internal space and the second internal space. A delivery cannula delivers the medicament into the skin of the patient. In one embodiment, a base has a bottom surface for orienting toward the skin of the patient and a top surface facing the internal space. The top surface of the base has one or more integrally formed fluid channels disposed therein.

The delivery device can have a housing and a base enclosing the housing to form an internal cavity for receiving the pump mechanism and other operating components for the delivery device. The delivery device is particularly suitable for delivering insulin at a controlled rate through a cannula or catheter to the patient. The delivery device is shown as a patch pump or infusion pump although the delivery device can have other forms, such as pump mechanism for use with an infusion set. At least one surface of the housing or the base has an integrally formed fluid channel to deliver the insulin from one component of the delivery device to the cannula or catheter The fluid channel can be formed as an open channel that is molded on a surface of the base of the device. The fluid channel has an opening at an inlet end and an opening at the outlet end passing through the base to a side opposite the open channel where the openings can be connected to a component of the device and to the cannula or catheter. A flexible membrane, such as a flexible film or layer is applied to the surface of the base overlying the open channel to enclose the open channel and form the fluid channel. A cam mechanism sequentially engages a cam follower, such a stamped metal cam follower, to deflect the membrane in a controlled sequence to create the pumping action in the fluid channel and propel the fluid from the inlet end to the outlet end.

In one embodiment, the delivery device for delivering a medicament to a patient includes a housing having an open end and a base coupled to the open end and defining an inner cavity. A reservoir containing the medicament is provided in the cavity of the housing. A delivery mechanism, such as a cannula or catheter, and a pump mechanism are connected to the reservoir. The base has an integrally formed fluid channel having a flexible membrane enclosing recess in the base forming the flow path in fluid communication with the reservoir and the delivery mechanism. The flexible membrane is deflected by cam and cam follower where the cam follower is stamped metal sheet having a protrusion engaging the flexible membrane.

Additional and/or other aspects and advantages of the present delivery device is set forth in the description that follows or will be apparent from the description, or may be learned by practice of the invention. The present invention may comprise delivery devices and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various aspects and advantages of embodiments of the delivery device will be more readily appreciated from the following detailed description, taken in conjunction with the accompanying drawings, of which.

DETAILED DESCRIPTION OF EMBODIMENTS

Figure 1:
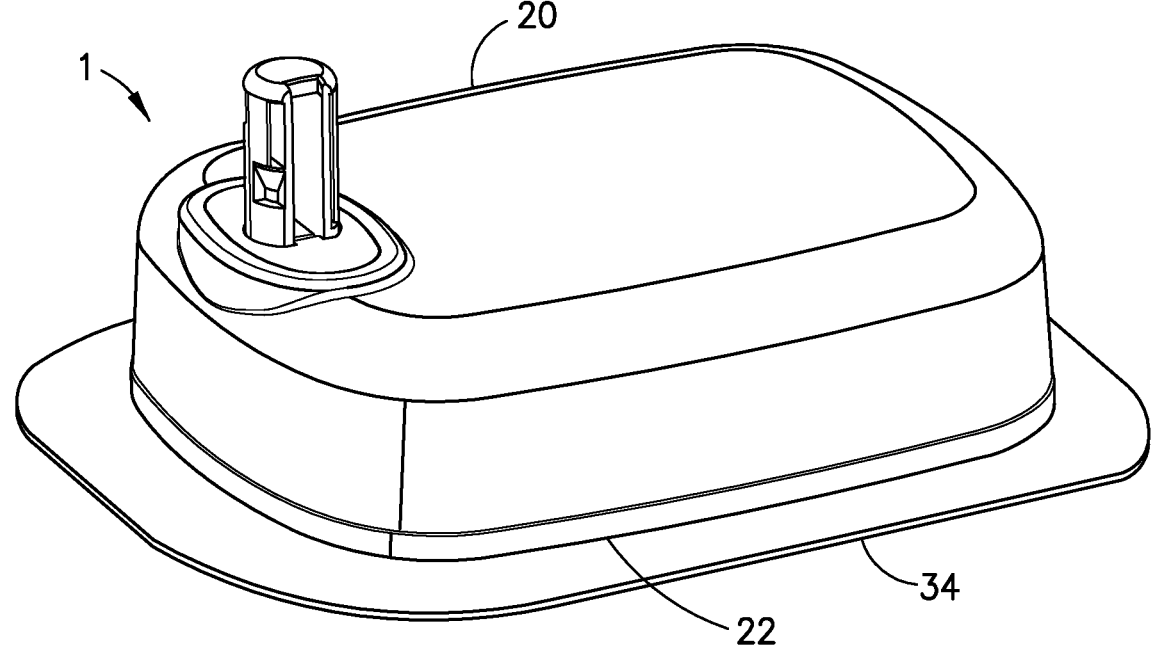
FIG. 1 is a perspective view of a delivery device constructed in accordance with an illustrative embodiment.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting. Any of the embodiments and/or elements and features disclosed herein may be combined with one another to form various additional embodiments not specifically disclosed, as long as they do not contradict or are not inconsistent with each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

The illustrative embodiments are described with reference to diabetes management using insulin therapy. It is to be understood that these illustrative embodiments can be used with different drug therapies and regimens to treat physiological conditions other than diabetes using different medicaments other than insulin.

Figure 2:
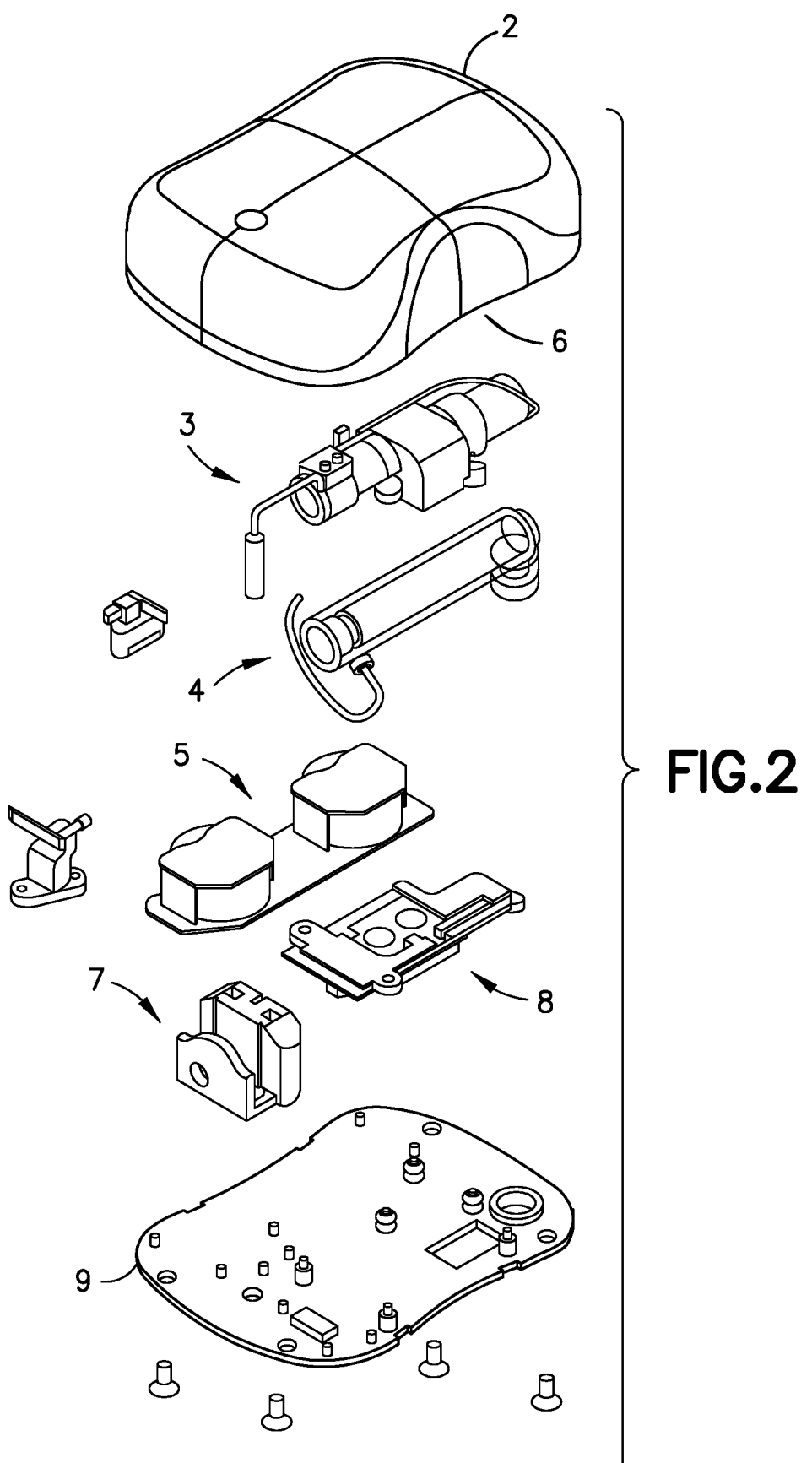
FIG. 2 is an exploded view of the various components of the delivery device of FIG. 1.

FIG. 1 is a perspective view of an exemplary embodiment of a medicament delivery device. In one embodiment, the delivery device is shown as a patch pump 1. In other embodiments, the delivery device can have other structures and delivery mechanisms, such as an infusion set and pump arrangement. The delivery device as described herein is configured for delivering insulin in the form of an insulin solution to a patient at a controlled rate. FIG. 2 is an exploded view of the various components of the patch pump of FIG. 1, illustrated with a housing forming a main cover. The various components of the patch pump 1 include: a reservoir 4 for storing insulin, a pump 3 for pumping insulin out of the reservoir 4, a power source 5 in the form of one or more batteries, an insertion mechanism 7 for inserting an inserter needle with a cannula into a user's skin, and control electronics 8 in the form of a circuit board with optional communications capabilities to outside devices such as a remote controller and computer, including a smart phone; a pair of dose buttons on the housing 20 for actuating an insulin dose, including a bolus dose. A base 22 for supporting the components may be attached to the housing by suitable fasteners or snap connectors. The patch pump 1 also includes various fluid connector lines that transfer insulin pumped out of the reservoir 4 to the infusion site. The cannula can be a rigid cannula or flexible catheter as known in the art.

The wearable medical delivery device (e.g., insulin delivery device (IDD) such as patch pump 1 can be operable in conjunction with a remote controller that communicates wirelessly with the pump 1 that can include a graphical user interface (GUI) display for providing a user visual information about the operation of the patch pump 1 such as, for example, configuration settings, an indication when a wireless connection to the patch pump is successful, and a visual indication when a dose is being delivered, among other display operations. The display can include a touchscreen display that is programmed to allow a user to provide touch inputs such as a swipe to unlock, swipe to confirm a request to deliver a bolus, and selection of confirmation or settings buttons, among other user interface operations.

The delivery device shown as a patch pump 1 has a main cover that forms the housing 20 with an internal cavity. The base 22 carries and supports various components as described below. A hermetic seal between the cover and the base prevents fluid ingress and prevents other particles from passing the seal. Embodiments of the delivery device also includes a vent or a vent membrane to provide pressure equalization between the interior of the housing and the exterior atmosphere.

Figure 3:
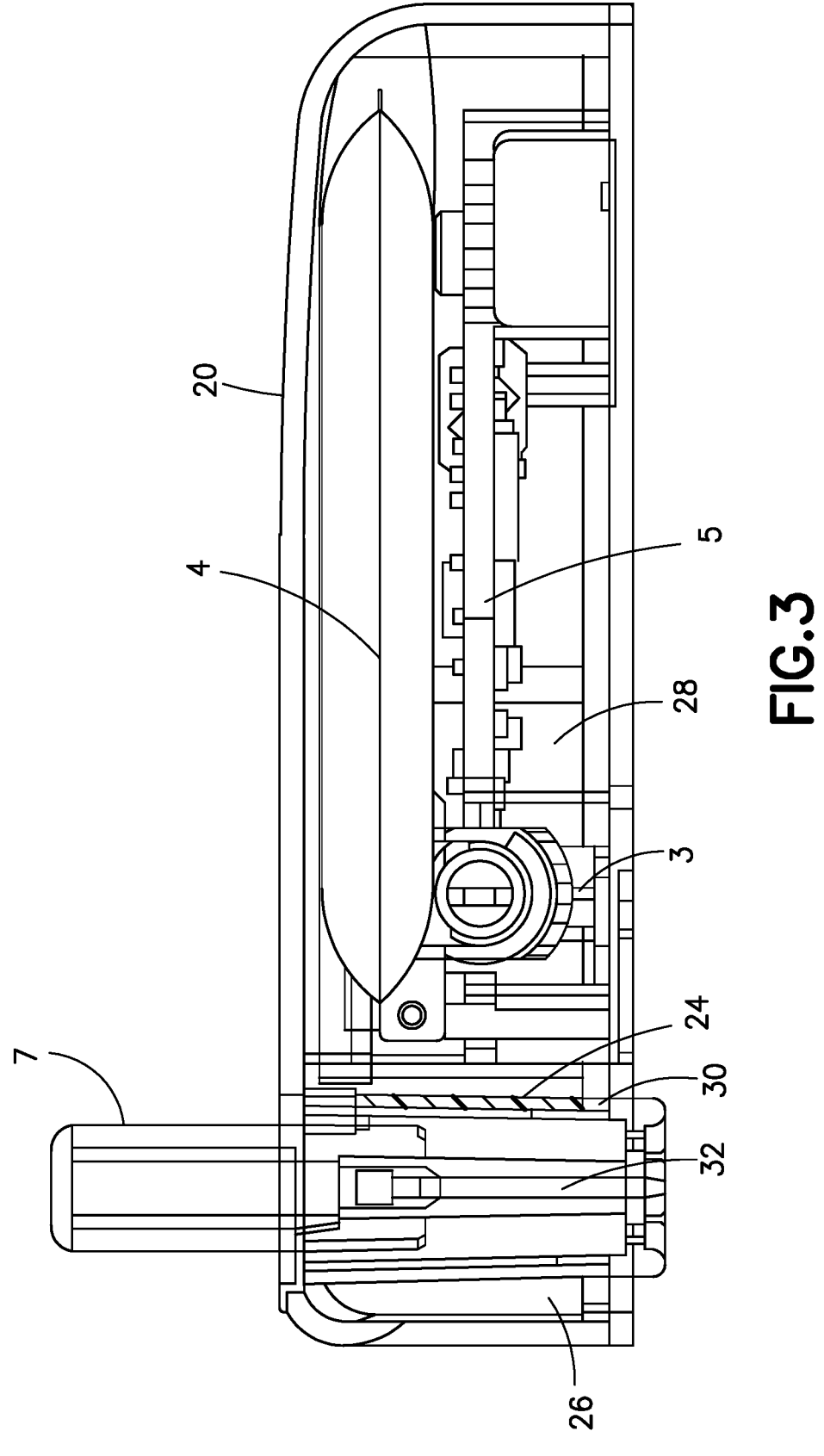
FIG. 3 is a side view in cross section of the delivery device.

Referring to FIG. 3, the housing 20 and the base 22 define an interior cavity divided by a wall forming a barrier 24 into a first internal space 26 forming a first cavity and a second internal space 28 forming a second cavity. The barrier 24 can be part of the housing or cover and integrally formed as a unitary structure with the cover. Alternatively, the internal barrier can be formed with the base or can be formed as a separate unit coupled to the base and the cover. In the embodiment shown, the barrier 24 is preferably sealed to a protruding rib 30 on the base 22 such that the interface between the barrier 24 and the rib 30 is hermetically joined using an appropriate sealing method. The barrier 24 separates the first internal space 26 from the second internal space 28 and protects the first internal space from fluid ingress from the second internal space. According to one embodiment, the second internal space is not sealed from fluid ingress.

The first internal space 26 includes components such as the pump mechanism 36, the force sensing resistor, and the electronics for controlling the operation of the delivery device and controlling and monitoring the delivery of the medication to the patient. Examples of the electronics include semiconductor chips, controllers, diodes, antennas, coils, batteries, other components (resistors and capacitors, for example) and circuit boards used to operate and control the patch pump 1 and operate the pump. As readily understood by the skilled artisan, it is desirable to have a dry environment for proper operation of these components, particularly the electronics. The second internal space 28 includes the insertion mechanism 7 and the delivery assembly such, as a cannula 32. According to one embodiment, the insertion mechanism 7 interfaces with the skin of a patient and the second internal space 28 can be neither a hermetically sealed environment, nor a liquid-tight environment. Various insertion mechanisms can be used as known in the art.

According to one embodiment, the components of the first internal space 26 are different from the components of the second internal space 28. Alternatively, the first internal space and the second internal space can share some of the same components. For example, in some embodiments, portions of the reservoir 4 are disposed in both the first and second internal spaces. When the reservoir and the insertion mechanism 7 are separated by the barrier 24, the two internal spaces fluidly communicate for effective operation of the delivery device and the transfer of fluid from the reservoir and the pump mechanism.

The delivery device can include a fill port connected to a conduit for supplying the medicament to the reservoir 4. The fill port can be disposed in the first internal space 26 or the second internal space 28, but is typically located in the first internal space 26. In some embodiments, the fill port includes a portion that serves as part of the flow path for medicament exiting the reservoir 4.

During use, the bottom surface of the delivery device is oriented toward the skin of the patient. In some embodiments, the bottom surface includes an adhesive that removably attaches the base to the skin of the patient. Alternatively, an adhesive pad 34, as illustrated in FIG. 1, adheres to both the bottom surface and the skin of the patient. Typically, 3M™ medical tape (e.g. product no. 1776) is the adhesive used, although various types of known industry adhesives can be used. The adhesive is selected to ensure compatibility with human skin to prevent undesired reactions. Also, compatibility of the adhesive and the insulin is considered in case that the adhesive and the insulin accidentally mix.

Figure 4:
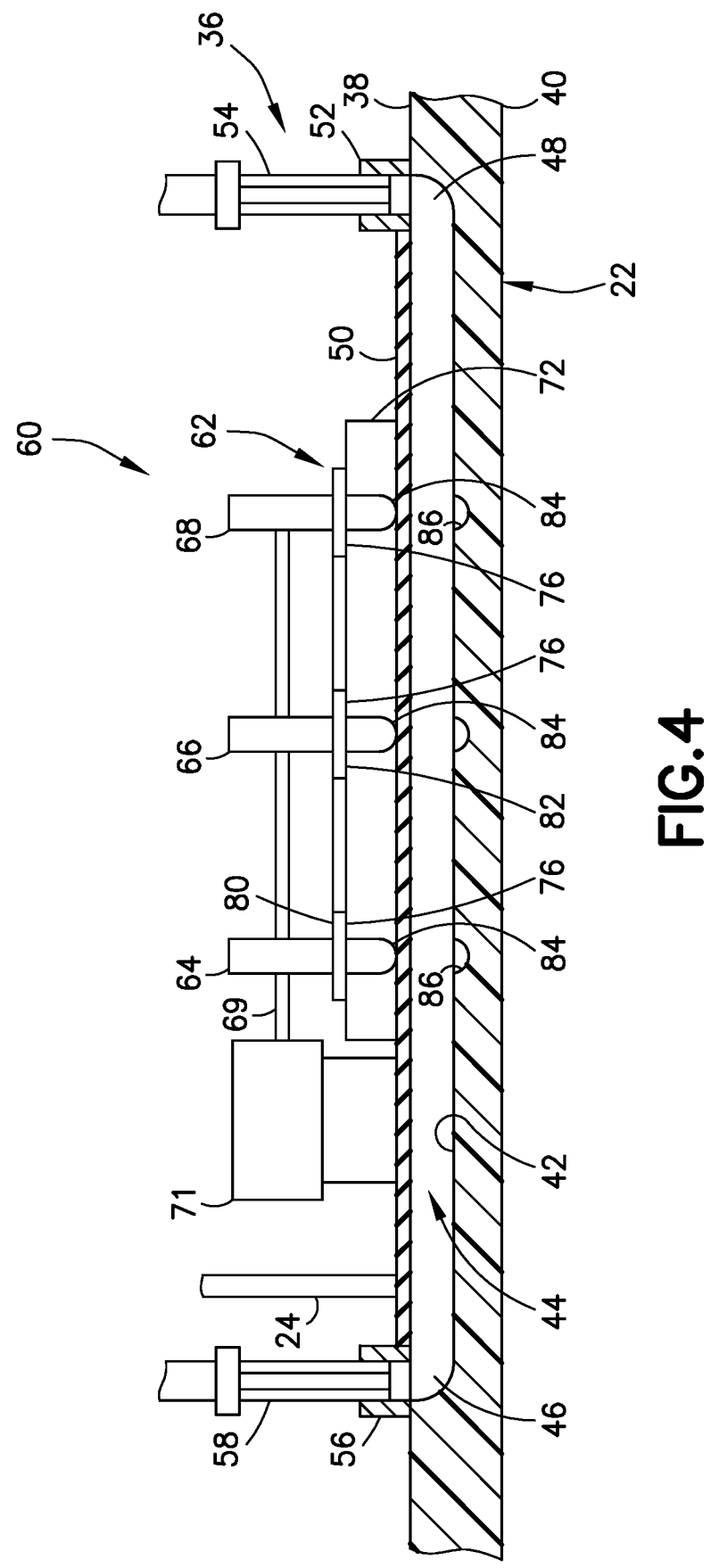
FIG. 4 is a side view of the fluid channel and cam assembly in one embodiment.

The pump mechanism 36 in one embodiment is peristaltic pump for delivering the medication, such as insulin, from the reservoir to the delivery assembly, such as the cannula 32 or flexible catheter. The pump mechanism 36 is formed with at least one component part of the delivery device. In the embodiment disclosed, the pump mechanism 36 is formed with the base 22. As shown in FIG. 4, the base 22 has a top surface 38 facing the internal cavity 28 and a bottom surface 40 facing outwardly for contacting the patient during use. The delivery mechanism, such as a cannula, projects from the bottom surface 40 where the cannula is inserted into the patient to a selected depth for delivering the medication to the intended depth and location in the patient.

As shown in FIG. 4, the top surface 38 of the base 22 includes at least one recess 42 for forming a fluid channel 44 through the base 22 from a first location to a second location. The recess 42 forming the fluid channel 44 can have a substantially U-shape or groove shape with a longitudinal dimension extending parallel to the plane of the base 22. In the embodiment shown, the recess 42 has an open side facing outward from the top surface 38. The fluid channel 44 extends in a longitudinal direction parallel to the plane of the base 22 and is configured and located to direct a fluid from a first location in the device to a second location in the device. In the embodiment shown, the fluid channel 44 is formed by the recess 42 having an inlet end 46 and an outlet end 48. The recess 42 forming the fluid channel 44 in the embodiment shown is molded in the top surface 38 of the base 22. The fluid channel 44 is configured where the inlet end 46 communicates with the reservoir to receive the medication and the outlet end 48 communicates with the delivery mechanism, such as the cannula 32.

The fluid channel 44 is enclosed by a flexible membrane 50 to enclose the recess 42 and form a fluid tight channel between the base 22 and the membrane 50 for the fluid passing between the components and between the inlet end 46 and the outlet end 48. The flexible membrane 50 can be a flexible sheet or film bonded to the top surface 38 to overly and cover the recess as shown in FIG. 4 to form a fluid tight path for the medicament. The membrane 50 has a shape to conform the top surface 38 of the support and the recess that forms the channel. In the embodiment shown, the top surface 38 of the support is substantially flat and the membrane 50 is substantially flat. The membrane 50 has a bottom surface attached to the top surface of the base 22 and a top surface facing away from the base 22.

In the embodiments shown, the recess is formed in the base 22 on the top surface facing the cavity of the delivery device. In other embodiments, a separate plate can be provided with the recess formed in a top surface of the plate. The plate can then be coupled to the base by a suitable attachment mechanism.

A coupling 52 is formed on the top surface 38 at the outlet end 48 of the fluid channel 44 with an open end for receiving a flexible conduit 54. In the embodiment shown, the conduit extends between the outlet end of the channel to the cannula 32 of the insertion mechanism for supplying the cannula with the medicament and delivering to the patient. The cannula of the delivery device has a lumen for introducing the medicament into the patient. The cannula can be hollow steel cannula or a flexible catheter as known in the art.

A coupling 56 on the top surface 38 at the inlet end 46 of the fluid channel 44 communicates with the fluid channel. In the embodiment shown, the coupling 56 receives a conduit 58 that extends between the reservoir and the channel for supplying the medicament from the reservoir to the inlet of the fluid channel. In the embodiment shown, the fluid channel extends parallel to a plane of the base 22 for directing the fluid between two spaced-apart locations on the top face of the base. The fluid channel is located and has a length to provide fluid communication between the operating components of the delivery device located in the cavity of the housing. In one embodiment, the channel is oriented or positioned so that the inlet end and the outlet end are on opposite sides of the barrier wall 24 to provide fluid communication between the first internal space 26 and the second internal space 28.

Figure 5:
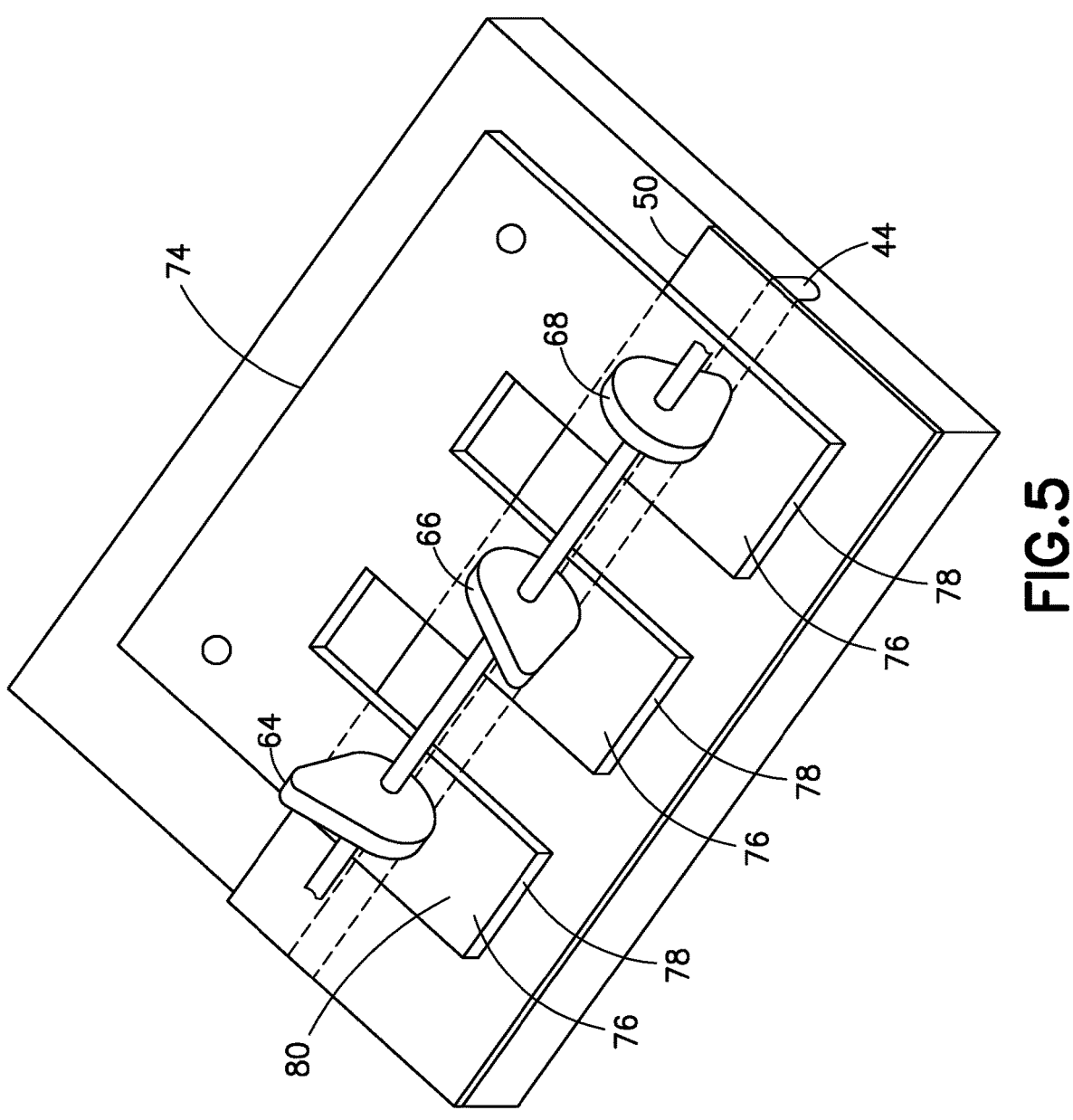
FIG. 5 is a perspective view of the pump mechanism of FIG. 3.

Referring to FIG. 4, the pump mechanism 36 includes a drive assembly including a cam assembly 60 and a cam follower assembly 62. The membrane 50 is attached to the top surface of the base 22 and is made of a flexible material, such as a flexible polymer, that can be deflected inwardly by the cam assembly. The cam assembly 60 in the embodiment shown includes a plurality of rotating cams 64, 66 and 68 mounted on a rotating drive shaft 69 that is supported by a suitable support to orient the cams and drive shaft in a position to operate the pump mechanism. The drive shaft 69 is connected to a drive motor 71 as shown. Each cam member 64, 66, 68 includes a lobe 70 oriented for actuating a cam follower of the cam follower assembly at a selected timing sequence to pump the fluid from the inlet end 46 to the outlet end 48. As shown in FIGS. 4 and 5, three cams 64, 66 and 68 are provided on the shaft 69. The lobes 70 of each cam is oriented about 120° apart. In other embodiments, more than three cams can be provided where the lobes sequentially engage the membrane to pump the fluid through the fluid channel.

The cam follower assembly 62 is mounted on a support 72 coupled to the top surface 38 of the base 22 to support the cam follower assembly next to or adjacent the membrane 50 and the cam assembly 60. In the embodiment shown, the cam follower assembly 62 is a one-piece member having separate members for engaging a respective cam 64, 66, and 68 and for engaging the membrane 50. The cam follower assembly 62 can be made of a stamped metal having sufficient flexibility to deflect when actuated by the respective cam 64, 66, and 68. The flexibility of the cam follower assembly enables efficient contact with the membrane 50 to deflect the membrane to close the fluid channel. In other embodiments, the membrane can be made of shape memory alloy that can be actuated the cam assembly.

The cam follower assembly 62 as shown has a body portion 74 coupled to the support 72 and a plurality of flexible portions shown as flexible legs 76 extending from the body portion 74. In the embodiment shown, the legs 76 extend in a plane parallel with the plane of the body portion 74. In other embodiments, the legs 76 can be independent of the body portion and formed by separate members independently supported by a suitable support. In the embodiment shown, the legs 76 are cantilevered from the body portion 74 and are sufficiently flexible to deflect when contacted by the lobes 70 on the respective cam 64 to deflect the membrane 50. The legs 76 have a distal end 78 with a top surface 80 for contacting the respective cam and a bottom surface 82 for contacting the membrane 50 at a specific location along the length of the fluid channel 44. The bottom surface 82 in the embodiment shown has an integrally formed protrusion 84 with a shape and dimension complementing the shape and dimension of the recess 42 that forms the fluid channel 44. In the embodiment shown, the protrusion 84 has a convex shape forming a dome-like shape corresponding substantially to the cross sectional configuration of the recess.

As shown in FIG. 4, the recess 42 has a plurality of spaced-apart recessed wells 86 formed in a bottom surface of the recess. Each well 86 is spaced apart a distance corresponding to the spacing of the cams 64, 66, and 68, and spaced corresponding to the location of the protrusions 84 of the cam follower assembly 62. The shape and dimension of the wells 86 complement the shape and dimension of the protrusions 84. During the operation of the delivery device, the shaft 69 is rotated by the motor 71 to rotate the cams so that lobes 70 sequentially contact the membrane 50. The lobes 70 have a dimension to actuate the legs 76 of the cam follower assembly 60 so that the membrane is deflected inwardly to close the fluid channel in sequence and provide a peristaltic pumping action.

The membrane 50 is formed from a flexible material that can be depressed and deformed to the configuration of the fluid channel to close the fluid channel wen the cam actuates the respective can follower. The membrane can be, for example a plastic material, that has sufficient memory to return to its original configuration when the force by the cam follower is released to open the fluid channel. The cam follower is made of a material that has sufficient memory to return to its original shape and configuration to allow the membrane to return to its original configuration to open the channel.

Figures 6, 7:
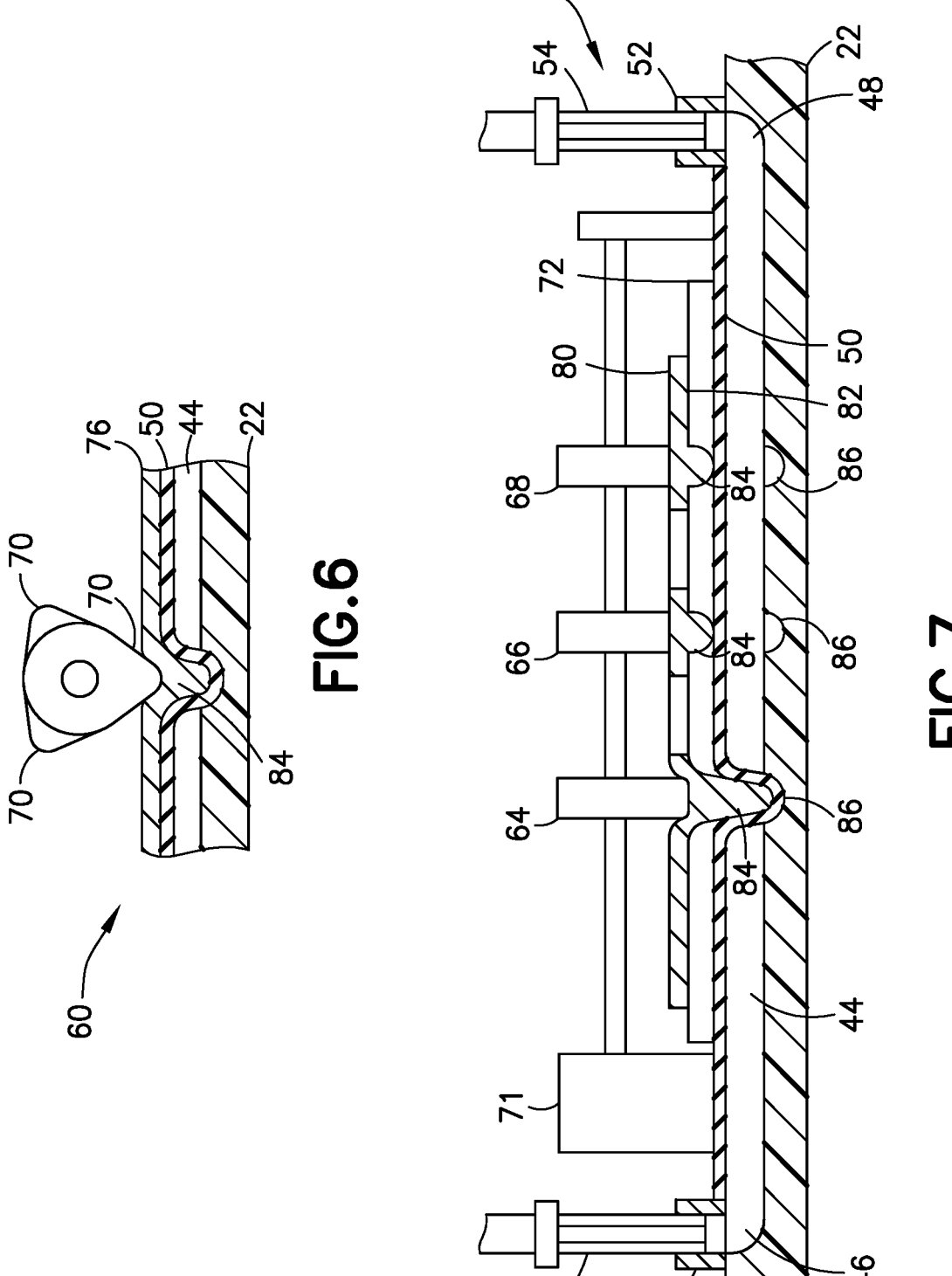
FIG. 6 is an end view in cross section of the pump mechanism of the delivery device of FIG. 5.
FIG. 7 is a side view in cross section of the pump mechanism showing the cams in a first position.
Figures 8, 9:
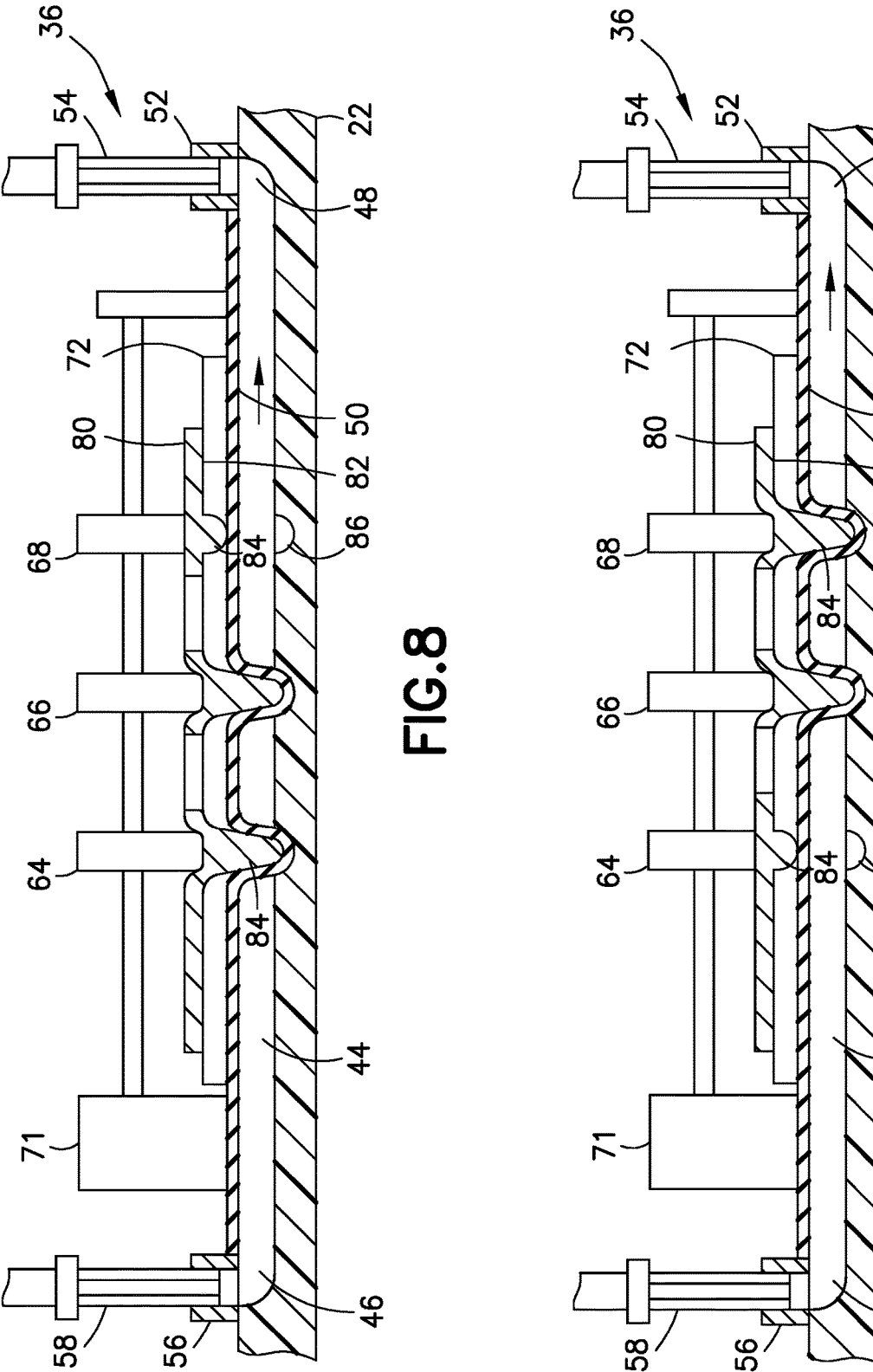
FIG. 8 is a side view in cross section of the pump mechanism showing the cams in a second position.
FIG. 9 is a side view in cross section of the pump mechanism showing the cams in a third position.

FIG. 7 shows the first cam 64 actuating the respective leg 76 of the cam follower assembly 62 to deflect the membrane 50 into the recess 42 to close the fluid channel. The cam 64 is configured to close the fluid channel for at least about 240° of rotation of the shaft. As shown in FIG. 8, the cam assembly is configured so that the second cam 66 rotates into contact with the respective leg of the cam follower assembly to actuate the cam follower to close the fluid channel at the point of the second cam 66 while the fluid channel is closed at the point of the first cam 64. The actuation of the second cam 66 to close the fluid channel forces the fluid in fluid channel toward the outlet end of the fluid channel in the direction indicated by the arrow in FIG. 8. As shown in FIG. 9, the third cam 68 then rotates into contact with the respective cam follower to deflect the membrane 50 to close the fluid channel at the point of the third cam 68 while the first cam 64 is rotated to a position to open the fluid channel and the second cam 66 remains in contact with the cam follower to retain the fluid passage closed at the location of the second cam. The actuation of the third cam while the fluid channel is closed at the location of the second cam forces the fluid toward the outlet end of the fluid channel in the direction of the arrow shown in FIG. 9. In this manner the rotation of the shaft 69 and the cams 64, 66, and 68 sequentially close and open of the fluid channel to pump the fluid through the fluid channel. The cams 64, 66, and 68 are configured and oriented on the shaft so that the fluid channel is always closed by one of the cams and cam followers to control the fluid flow in the direction toward the outlet end of the fluid channel.

Figure 10:
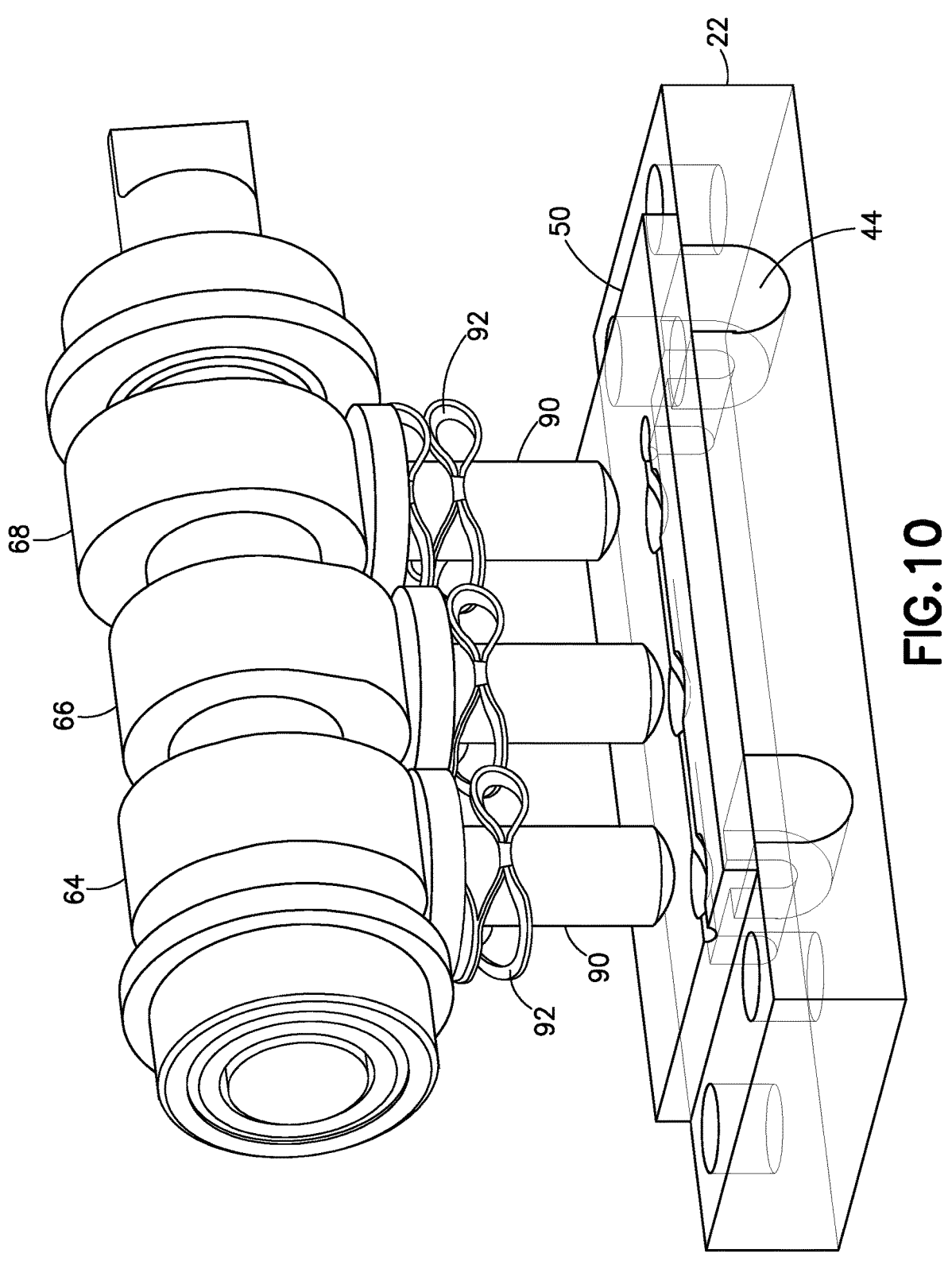
FIG. 10 is a perspective view of the pump mechanism in another embodiment.

FIG. 10 shows another embodiment of the pump mechanism. In this embodiment, separate cams and cam followers 90 are mounted in a suitable support for linear movement in a direction perpendicular to the plane of the membrane 50. Each of the cam followers 90 have a first end that contact the respective cam 64, 66, 68 and a second end contacting the flexible membrane 50. The rotation of the cams produce the sequential movement to depress the membrane and produce the peristaltic pumping action. As shown in FIG. 10, spring members 90 are provided to bias the cam followers 90 away from the membrane 50.

Figure 11:
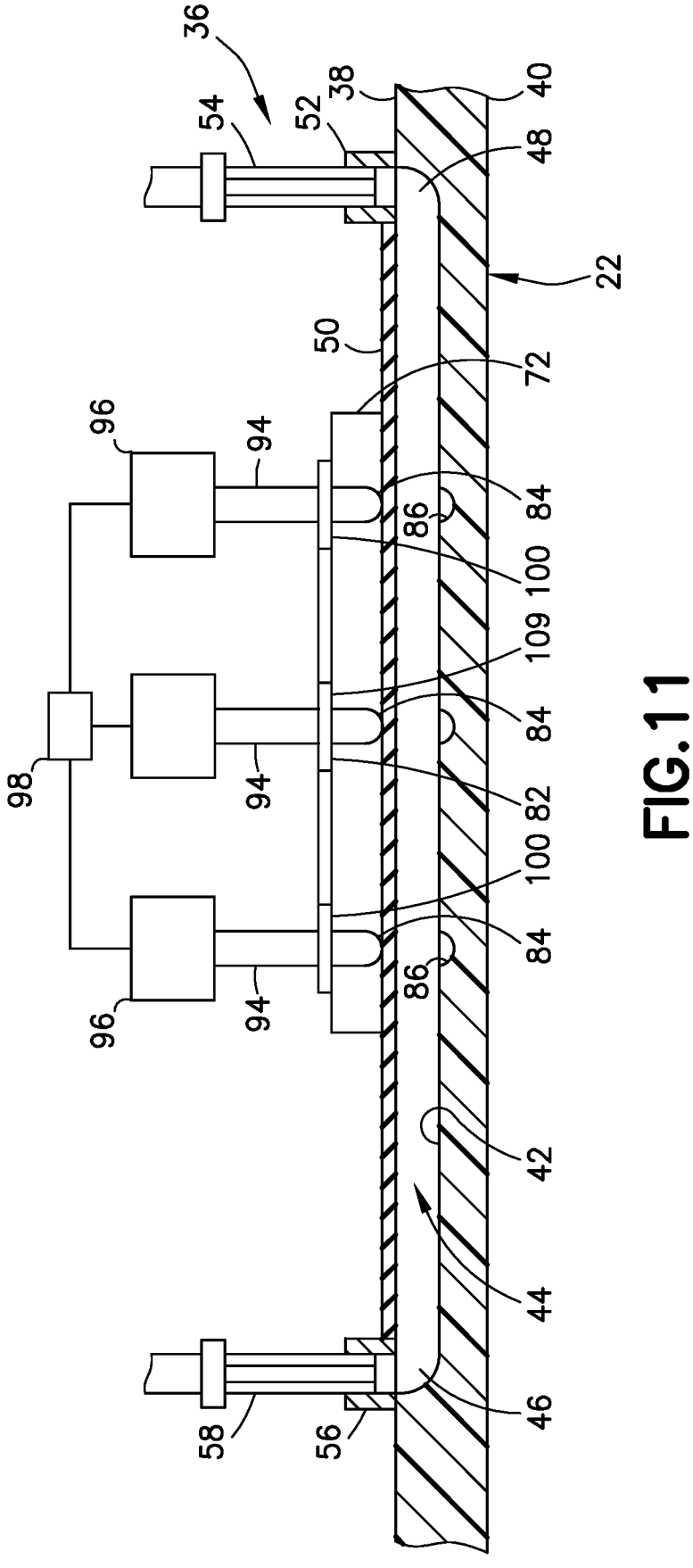
FIG. 11 is cross sectional view of a further embodiment of the pump mechanism.

FIG. 11 shows another embodiment of the pump mechanism where each of the cams are separate units that cooperate with separate cam followers. In the embodiment shown, each cam member 94 is operatively connected to a separate drive mechanism 96. The drive mechanisms 96 are connected to a control unit 98 to actuate the drive mechanisms 96 and the respective cam member 94 in the suitable sequence to produce the peristaltic pumping action. In this embodiment, each cam member is associated with a separate flexible membrane 100. The cam followers 100 cam be configured as in the previous embodiments. Each of the cam followers are configured to move in a linear direction perpendicular to the plane of the membrane and the longitudinal dimension of the fluid channel with no lateral or transverse movement relative to the membrane.

The pump assembly as shown, minimizes the number of different materials that contact the medication during the pumping action to increase stability, reduce shear stress and avoid contact of the medication with lubricants and metal or plastic parts of pump mechanism.

In the embodiment shown, the fluid channel is formed in a top surface of the base of the delivery device. In other embodiments, the fluid channel can be formed in a separate plate that can be mounted within the cavity of the delivery device or attached to the base or wall of the housing. The fluid channel and the pump mechanism can be formed as separate unit that is attached base or other part of the delivery device. The fluid channel can be formed in a support member that also supports the cam assembly and cam follower assembly, which can mounted within the housing of the delivery device. The delivery device can be constructed so that various components can be replace or discarded after use while some parts are reusable. In one example, the base supports the fluid channel which can be separated from the pump mechanism so that the pump mechanism can be retained and reused. The base is replaced after use to avoid contamination of the fluid channel between uses.

The delivery device is particularly suitable for delivering insulin to the patient over an extended period of time. The delivery device is actuated to insert the cannula 36 into the patient. The pump is actuated to carry the insulin at a controlled rate from the reservoir 4 to the cannula 36 where the insulin is introduced into the patient.

In the embodiment illustrated, the pump mechanism includes the micro-cam assembly and the micro-cam follower assembly for advancing the fluid medication through the fluid channel. In other embodiments, the pump assembly does not include the cam follower assembly so that the cam members contact the membrane directly to deflect the membrane into the fluid channel to produce the peristaltic pumping action.

As shown in the drawings, the fluid channel can extend below the barrier wall 24 between the first interior area 26 and the second interior area 28. In this manner, the fluid channel is able to carry the fluid or medication between the different enclosed areas without passing directly through the barrier 24.

The fluid channels are recessed from (or inscribed into) the surface of the base by a molding process, such as injection molding, or by a cutting process, such as milling. In other embodiments, the fluid channels are disposed on the main cover of the housing, or on the base within the inner cavity of the housing. Similar fluid channels can be positioned in a plurality of locations in the device. The cross-sectional shape and dimension of the fluid channels is defined by the desired flow characteristics. Exemplary cross-sectional profiles of the fluid channels include square, rectangular, and semi-circular. One skilled in the art will appreciate that other cross-sectional profiles can be used without departing from the scope of the present invention.

Although only a few embodiments of the present device are shown and described, the present device is not limited to the described embodiments. Instead, it will be appreciated by those skilled in the art that changes may be made to these embodiments without departing from the principles and spirit of the device. Different embodiments can be combined with other embodiments as long as they are not inconsistent with each other. It is particularly noted that those skilled in the art can readily combine the various technical aspects of the various elements of the various exemplary embodiments that have been described above in numerous other ways, all of which are considered to be within the scope of the disclosure and equivalents thereof.

The invention claimed is:

1. A delivery device for a medicament comprising:
   a housing having a base, said housing having an internal cavity enclosing a medication reservoir, a delivery mechanism connected to the medication reservoir and configured for delivering the medication to a patient, and a peristaltic pump mechanism oriented between said medication reservoir and said delivery mechanism;
   said peristaltic pump mechanism comprising an open recess formed on a surface of said base forming a fluid channel extending between a first end communicating with said medication reservoir and a second end communicating with said delivery mechanism, a flexible membrane on said base and enclosing said recess to form said fluid channel, and an actuator assembly having a plurality of actuators sequentially deflecting said membrane toward said base and into said fluid channel to direct the medication from said reservoir to said delivery mechanism.

2. The delivery device according to claim 1, wherein said base has a top surface facing said internal cavity and a bottom surface configured for contacting a patient, and where said open recess is formed in said top surface.

3. The delivery device according to claim 2, wherein said peristaltic pump mechanism is oriented within said cavity.

4. The delivery device according to claim 3, wherein said flexible membrane comprises a sheet material having a top surface and a bottom surface, said inner surface coupled to said surface of said base to enclose said open recess and said top surface facing said peristaltic pump mechanism.

5. The delivery device according to claim 4, wherein said peristaltic pump mechanism includes a cam assembly and said actuator assembly comprises a cam follower assembly, said cam follower assembly engaging said flexible membrane to force fluid in said fluid channel from said inlet end to said outlet end.

6. The delivery device according to claim 5, wherein said cam follower assembly includes a base portion coupled to said base, and plurality of flexible legs extending from said base portion, each said legs configured for contacting said membrane to deflect the membrane inwardly to close the fluid channel.

7. The delivery device according to claim 6, wherein said cam assembly includes a plurality of cam members configured for engaging a respect leg of said cam follower assembly.

8. The delivery device according to claim 7, wherein each said leg of said cam follower assembly has a top surface configured for contacting a respect cam of said cam assembly, and a bottom surface configured for contacting and deflecting the membrane.

9. The delivery device according to claim 8, wherein said bottom surface of said legs of said cam follower assembly has a protrusion extending toward said membrane and is configured for deflecting said membrane and closing said fluid channel.

10. The delivery device of claim 9, wherein said cam members sequentially contact a respective leg of the cam follower assembly to sequentially close the fluid channel to force the fluid in the fluid channel from the inlet end to the outlet end.

11. The delivery device of claim 1, wherein said housing further comprises a barrier wall defining a first interior area and a second interior area, and where said fluid channel extends between said first interior area and said second interior area.

12. The delivery device of claim 1, wherein said medication is insulin and said delivery mechanism includes a cannula having a distal end for penetrating the skin of the patient, and a proximal end, and a conduit extending between said proximal end of said cannula and said outlet end of said fluid channel.

13. A delivery device for delivering a medicament to a patient, said delivery device comprising:

a housing having an interior cavity and a base enclosing said cavity, a reservoir within said cavity for containing the medicament, a delivery mechanism having a cannula for delivering the medicament to the patient, said base having a top surface facing said interior cavity with a longitudinally extending recess and a bottom surface configured to attaching to the skin of a user, and a flexible membrane on said top surface covering said recess and forming a fluid channel;

a pump mechanism in said cavity for directing the medicament from said reservoir to said cannula, said pump mechanism including a cam assembly having a plurality of cam members and a cam follower assembly, said cam follower assembly including a plurality of flexible portions having a protrusion oriented to sequentially deflect said membrane inwardly into said fluid channel to close said fluid channel and force fluid in said fluid channel from an inlet to an outlet of said fluid channel.

14. The delivery device according to claim 13, wherein said cam assembly includes a plurality of rotating cam members, and said cam follower assembly includes a base portion coupled to said base, and said plurality of said flexible legs actuated by a respective cam member.

15. The delivery device according to claim 13, wherein said cam follower assembly is a stamped metal component.

16. The delivery device according to claim 13, wherein said cam follower assembly comprises a plurality of flexible cam follower members, each of said cam members coupled to said support.

17. The delivery device according to claim 13, wherein said cam assembly of said pump mechanism comprises a plurality of cam members having an associated drive mechanism, and said cam follower assembly comprises a plurality of cam follower members coupled to said support.

18. The delivery device according to claim 13, wherein said housing further comprises a barrier wall defining a first interior area and a second interior area, and where said fluid channel extends between said first interior area and said second interior area.

* * * * *